United States Patent
Beckert et al.

(10) Patent No.: US 6,632,454 B2
(45) Date of Patent: Oct. 14, 2003

(54) MULTILAYER PHARMACEUTICAL PRODUCT FOR RELEASE IN THE COLON

(75) Inventors: Thomas Beckert, Darmstadt (DE); Hans-Ulrich Petereit, Darmstadt (DE); Vishal K. Gupta, Evanston, IL (US)

(73) Assignee: Roehm GmbH & Co. KG, Darmstadt (DE)

( * ) Notice: Subject to any disclaimer, the term of this patent is extended or adjusted under 35 U.S.C. 154(b) by 0 days.

(21) Appl. No.: 09/926,567

(22) PCT Filed: Mar. 9, 2001

(86) PCT No.: PCT/EP01/02678

§ 371 (c)(1),
(2), (4) Date: Nov. 19, 2001

(87) PCT Pub. No.: WO01/68058

PCT Pub. Date: Sep. 20, 2001

(65) Prior Publication Data

US 2002/0192282 A1 Dec. 19, 2002

(30) Foreign Application Priority Data

Mar. 17, 2000 (DE) .......................................... 100 13 029

(51) Int. Cl.⁷ .............................. A61K 9/58; A61K 9/32
(52) U.S. Cl. .................. 424/482; 424/463; 424/474; 424/439; 424/451; 424/464; 424/462; 424/497
(58) Field of Search ................................ 424/463, 474, 424/482, 439, 451, 464, 462, 497

(56) References Cited

U.S. PATENT DOCUMENTS 6,156,340 A * 12/2000 Adeyeye et al. ............ 424/463

FOREIGN PATENT DOCUMENTS

DE      197 41 114      3/1999
WO      WO 01/15667     3/2001

OTHER PUBLICATIONS

V. K. Gupa, et al., Drug Development and Industrial Pharmacy, pp. 207–215, "Investigation of Potential Ionic Interactions Between Anionic and Cationic Polymethacrylates of Multiple Coatings of Novel Colonic Delivery System", 2002.*

V. K. Gupa, et al., International Journal of Pharmaceutics, pp. 83–91, "A Novel Ph– and the Time–Based Multi–Unit Potential Colonic Drug Delivery System. I. Development", 2001.*

V. K. Gupa, et al., International Journal of Pharmaceutics, pp. 93–102, "A Novel Ph– and Time–Based Multi–Unit Potential Colonic Drug Delivery System. II. Optimization of Multiple Response Variable", 2001.*

V.K. Gupa, et al., Proceedings 27$^{th}$ International Symposium on Controlled Release of Bioactive Materials, pp. 453–454, "Statistical Optimization of a Novel Mulit–Unit Colonic Delivery System Containing Multiple Coatings of Aqueous Polymethacyraltes", Jul. 7, 2000.*

* cited by examiner

Primary Examiner—James M. Spear
Assistant Examiner—Rachel M. Bennett
(74) Attorney, Agent, or Firm—Oblon, Spivak, McClelland, Maier & Neustadt, P.C.

(57) ABSTRACT

The invention relates to the use of a multilayer pharmaceutical product that substantially comprises a) a core containing a pharmaceutically active substance, b) an inner coating consisting of a copolymer or a mixture of copolymers that are composed of 85 to 98 wt.-% of radically polymerized C1 to C4 alkyl esters of the acrylic or methacrylic acid and 15 to 2 wt.-% of (meth)acrylate monomers with a quaternary ammonium group in the alkyl group, and c) an outer coating consisting of a copolymer that is composed of 75 to 95 wt.-% of radically polymerized C1 to C4 alkyl esters of the acrylic or methacrylic acid and 5 to 25 wt.-% of (meth)acrylate monomers with an anionic group in the alkyl group. The inventive product is used for producing a pharmaceutical product that releases the active substance contained therein according to the USP release test, at pH 1.2 during 2 hours and subsequent rebuffering to pH 7.0, by less than 5% after 2.0 hours after start of the test and by 30 to 80% after eight hours after start of the test.

8 Claims, 2 Drawing Sheets

MULTILAYER PHARMACEUTICAL PRODUCT FOR RELEASE IN THE COLON

Figure 1:
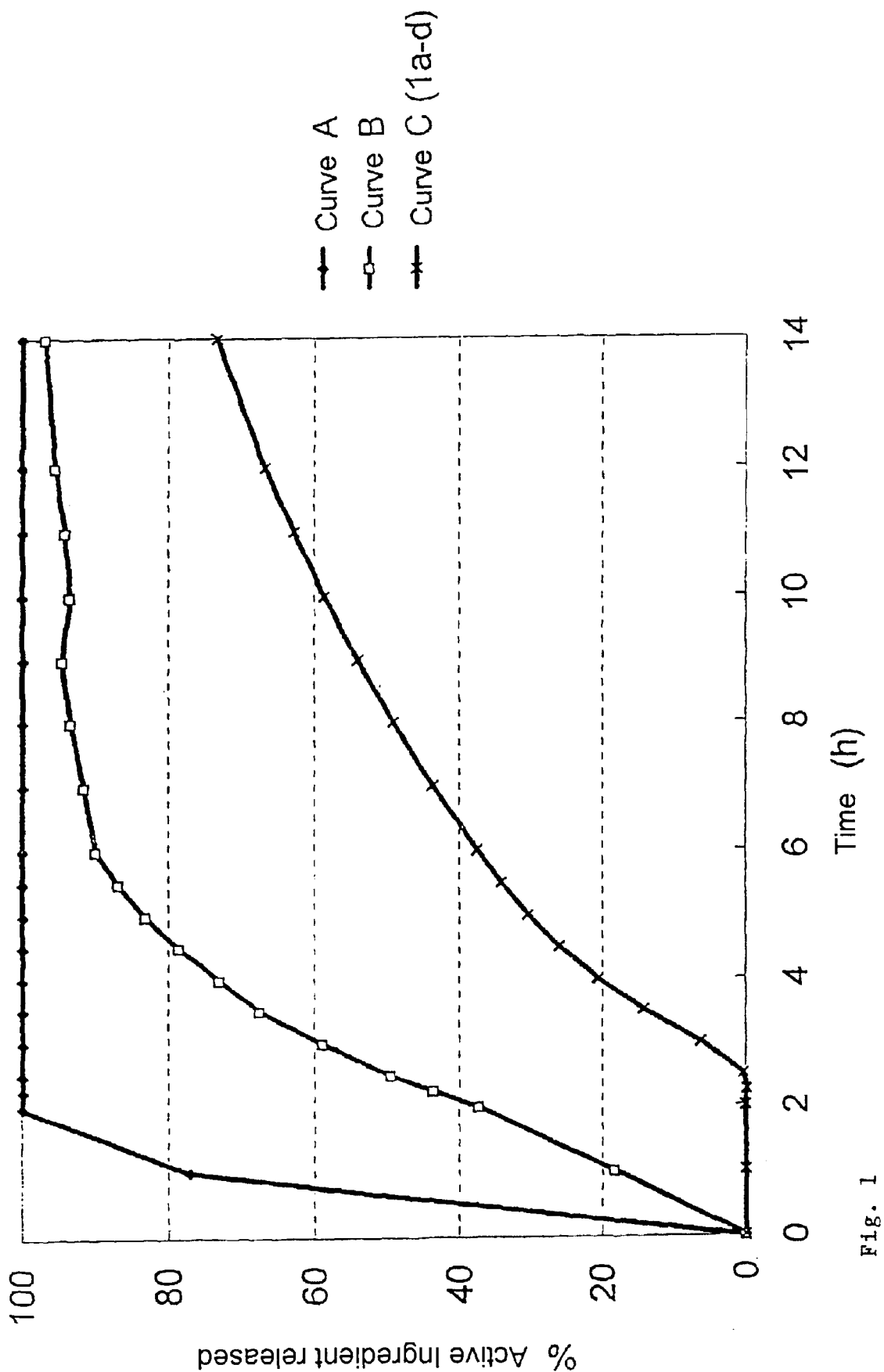

This application is a 371 of PCT/EP01/02678 filed Mar. 9, 2001.

The invention relates to a multilayer drug form composed of a core with an active pharmaceutical ingredient, of an inner polymer coating and of an outer polymer coating.

PRIOR ART (Meth)acrylate copolymers which comprise monomers with quaternary ammonium groups, e.g. trimethylammoniumethyl methacrylate chloride, and their use for release-slowing medicament coatings have been known for a long time (for example from EP-A-181 515 or from DE 1 617 751). Processing takes place in organic solution or as aqueous dispersion, for example by spraying onto medicament cores or else without solvent in the presence of flow aids by application in the melt (see EP-A-0 727 205).

EP-A 629 398 describes pharmaceutical formulations which have a core with an active ingredient and an organic acid, where the core has a two-layer covering. The inner covering in this case is formed by a release-slowing (meth)acrylate copolymer with quaternary ammonium groups (EUDRAGIT® RS), while the outer covering has an enteric coating, for example a copolymer of the type EUDRAGIT® L30D-55 (ethyl acrylate/methacrylic acid, 50:50). The release characteristics achieved can be described by a rapid release of active ingredient after a time lag at elevated pH.

EP 0 704 207 A2 describes thermoplastic materials for drug coverings soluble in intestinal juice. These comprise copolymers of 16 to 40% by weight acrylic or methacrylic acid, 30 to 80% by weight methyl acrylate and 0 to 40% by weight of other alkyl esters of acrylic acid and/or methacrylic acid.

EP 0 704 208 A2 describes coating agents and binders for drug coverings soluble in intestinal juice. These comprise copolymers of 10 to 25% by weight methacrylic acid, 40 to 70% by weight methyl acrylate and 20 to 40% by weight methyl methacrylate. The description mentions not only monolayer coatings but also multilayer coating systems. These may consist of a core which comprises, for example, a basic or a water-sensitive active ingredient, have a sealing layer of another coating material such as cellulose ether, cellulose ester or a cationic polymethacrylate, for example of the EUDRAGIT® type, inter alia including EUDRAGIT® RS and RL, and are then additionally provided with the abovementioned covering soluble in intestinal juice.

PROBLEM AND SOLUTION

The intention was to provide a drug form which releases virtually no active ingredient in the stomach and enables uniform and long-lasting release of active ingredient in the intestine, in particular shortly before or only in the colonic region. The nature of the release of active ingredient is intended in particular to comply with the requirement that in the USP release test two hours at pH 1.2 and a subsequent change in the buffer to pH 7.0, the release of the active ingredient present is less than 5% in the period up to 2.0 hours after the start of the test and 30 to 80% at the time eight hours after the start of the test.

The problem is solved by the use of a multilayer drug form which is essentially composed of a) a core with an active pharmaceutical ingredient
b) an inner coating of a copolymer or of a mixture of copolymers composed of 85 to 98% by weight free-radical polymerized C1- to C4-alkyl esters of acrylic or methacrylic acid and 15 to 2% by weight (methy)acrylate monomers with a quaternary ammonium group in the alkyl radical and
c) an outer coating of a copolymer composed of 80 to 95% by weight free-radical polymerized $C_1$- to $C_4$-alkyl esters of acrylic or methacrylic acid and 5 to 25% by weight (meth)acrylate monomers with an anionic group in the alkyl radical, for producing a drug form for which, in the USP release test two hours at pH 1.2 and a subsequent change in the buffer to pH 7.0, the release of the active ingredient present is less than 5% in the period up to 2.0 hours after the start of the test and 30 to 80% at the time eight hours after the start of the test.

It has been found, surprisingly, that the active ingredient release profile of the inner coating after dissolution of the outer, enteric coating differs from an active ingredient release profile obtained when inner coating is employed without outer coating. On use of the structure known in principle from EP 0 704 208 A2 and EP-A 629 398, an unexpectedly slow, very constant active ingredient release is obtained.

On carrying out the USP release test two hours at pH 1.2 and a subsequent change in the buffer to pH 7.5 the release of the active ingredient present at the time six hours after the start of the test is only 30 to 80%. This is particularly advantageous in the therapy of disorders in which local increases in the pH may occur in parts of the colon, but it is also intended in these cases to avoid active ingredient release which is too fast, or it is intended to achieve delayed active ingredient release.

In addition, unexpectedly, active ingredient release takes place substantially independently of the thickness of the outer coating.

Evidently there is an interaction with the inner coating layer during dissolution of the outer coating layer. The previously undisclosed release profile increases the possibilities for the skilled worker in the formulation of novel drug forms. In particular, the release characteristics are advantageous for some active ingredient substances which are intended to be released in the intestine, in particular shortly before or only in the colonic region, as constantly as possible. The evidently only extremely slight effect of the thickness of the outer coating layer on the release profile increases the safety of use in relation to manufacturing tolerances.

MODE OF OPERATION OF THE INVENTION

The invention describes the use of a multilayer drug form for which, in the USP release test for two hours at pH 1.2 and a subsequent change in the buffer to pH 7.0, the release of the active ingredient present is less than 5% in the period up to 2.0 hours after the start of the test and 30 to 80%, in particular 40 to 70%, at the time eight hours after the start of the test.

The USP release test (according to USP XXIV, method B, modified test for enteric coated products) is known to the skilled worker. The test conditions are, in particular: paddle method, 100 revolutions per minute, 37° C.; pH 1.2 with 0.1 N HCl, pH 7.0 by addition of 0.2 M phosphate buffer and adjustment with 2 N NaOH.

The multilayer drug form to be used consists essentially of a core with an active ingredient, of an inner and of an outer coating. It is possible in the usual way for excipients in use in pharmacy to be present, but they are not critical for the invention.

Core with an Active Pharmaceutical Ingredient

Cores

Carriers or cores for the coatings are tablets, granules, pellets, crystals of regular or irregular shape. The size of granules, pellets or crystals is ordinarily between 0.01 and 2.5 mm, and that of tablets between 2.5 and 30.0 mm. The carriers normally contain 1 to 95% active ingredient and, where appropriate, further pharmaceutical excipients. The usual production processes are direct compression, compression of dry, moist or sintered granules, extrusion and subsequent rounding off, wet or dry granulation or direct pelleting (e.g. on plates) or by binding of powders (powder layering) on active ingredient-free beads (nonpareils) or active ingredient-containing particles.

Beside the active ingredient, the cores may contain further pharmaceutical excipients: binders such as lactose, cellulose and derivatives thereof, polyvinylpyrrolidone (PVP), humectants, disintegration promoters, lubricants, disintegrants, starch and derivatives thereof, sugar solubilizers or others.

The cores can be provided in the usual way with an active pharmaceutical ingredient by applying the appropriate active ingredient for example as active ingredient powder to carrier particles (nonpareils) by means of an aqueous binder. The active ingredient cores (pellets) can be obtained after drying and screening in the required size fraction (e.g. 0.7 to 1 mm). This process is referred to inter alia as powder layering.

Active Pharmaceutical Ingredients

The active pharmaceutical ingredient which can be employed for the process of the invention are intended to be used on in the human or animal body in order
1. to heal, to alleviate, to prevent or to diagnose diseases, ailments, physical damage or pathological symptoms.
2. allow the state, the condition or the functions of the body or mental states to be identified.
3. To place active substances produced by the human or animal body, or body fluids.
4. To defend against, to eliminate or to render innocuous pathogens, parasites or exogenous substances or
5. to influence the state, the condition or the functions of the body or mental states.

Drugs in use can be found in reference works such as, for example, the Rote Liste or the Merck Index. Examples which may be mentioned are 5-aminosalicylic acid, corticosteroids (budesonide), and proteins (insulin, hormones, antibodies). It is possible to employ according to the invention all active ingredients which comply with the desired therapeutic effect within the meaning of the above definition and have an adequate stability and whose activity can be achieved via the colon in accordance with the above points.

Important examples (groups and single substances) without a claim to completeness are the following:

analgesics, antibiotics, antidiabetics, antibodies chemotherapeutics, corticoids/corticosteroids anti-inflammatory agents, enzyme products hormones and their inhibitors, parathyroid hormones peptic agents, vitamins, cytostatics Active ingredients which should be particularly mentioned are those which are to be released as constantly as possible in the intestine, in particular shortly before or only in the colonic region. Thus, the active pharmaceutical ingredient may be an aminosalicylate, a sulfonamide or a glucocorticoid, in particular 5-aminosalicylic acid, olsalazine, sulfalazine, prednisone or budesonide.

Examples of Active Ingredients mesalazine
sulfasalazine
bethamethasone 21-dihydrogenophosphate
hydrocortisone 21-acetate
cromoglicic acid
dexamethasone
olsalazine Na
budesonide, prednisone
bismunitrate, karaya gum
methylprednisolone 21-hydrogen succinate
myhrr, coffee charcoal, camomile flower extract
10% suspension of human placenta

New Active Ingredients and Active Ingredients Under-going Development and Testing

Literature from Relevant Pharmaceutical Databases Known to the Skilled Worker balsalazide
orally administered peptides (e.g. RDP 58)
interleukin 6
interleukin 12
ilodecakin (interleukin 10)
nicotine tartrate
5-ASA conjugates (CPR 2015)
monoclonal antibody against interleukin 12
diethyldihydroxyhomospermine (DEHOHO)
diethylhomospermine (DEHOP)
cholecystokinin (CCK) antagonist (CR 1795)
15 amino acid fragment of a 40 kd peptide from gastric juice (BPC 15)
glucocorticoid analog (CBP 1011)
natalizumab
infliximab (REMICADE)
N-deacetylated lysoglycosphingolipid (WILD 20)
azelastine
tranilast
sudismase
phosphorothioate antisense ologonucleotide (ISIS 2302)
tazofelone
ropivacaine
5-lipoxygenase inhibitor (A 69412)
sucralfate

Inner Coating

The inner coating consists of a copolymer or a mixture of copolymers composed of 85 to 98% by weight free-radical polymerized C1–C4-alkyl esters of acrylic or methacrylic acid and 15 to 2% by weight (meth)acrylate monomers with a quaternary ammonium group in the alkyl radical.

Appropriate (meth)acrylate copolymers are disclosed, for example, in EP-A 181 515 or DE 1 617 751. They are polymers which are soluble or swellable independently of the pH and which are suitable for pharmaceutical coatings. A possible production process to be mentioned is bulk polymerization in the presence of a free-radical initiator dissolved in a monomer mixture. The polymer can likewise also be produced by a solution or precipitation polymerization. The polymer can be obtained in this way in the form of a fine powder, which is achievable in the case of bulk polymerization by grinding, and in the case of solution and precipitation polymerization for example by spray drying.

Preferred C1- to C4-alkyl esters of acrylic or methacrylic acid are methyl acrylate, ethyl acrylate, butyl acrylate, butyl methacrylate and methyl methacrylate. The particularly preferred (meth)acrylate monomer with quaternary ammonium groups is 2-trimethylammoniumethyl methacrylate chloride.

A suitable copolymer can be produced, for example, 93 to 98% by weight free-radical polymerized C1- to C4-alkyl esters of acrylic or methacrylic acid and 7–2% by weight 2-trimethylammoniumethyl methacrylate chloride. Examples of possible contents in this case are 50–70% by weight methyl methacrylate, 20–40% by weight ethyl acrylate.

A corresponding copolymer is composed, for example, of 65% by weight methyl methacrylate, 30% by weight ethyl acrylate and 5% by weight 2-trimethylammoniumethyl methacrylate chloride (EUDRAGIT® RS).

A further suitable copolymer can be produced, for example, from 85 to less than 93% by weight free-radical polymerized C1- to C4-alkyl esters of acrylic or methacrylic acid and 15 to more than 7% by weight 2-trimethylammoniumethyl methacrylate chloride. Examples of possible contents in this case are 50–70% by weight methyl methacrylate, 20–40% by weight ethyl acrylate.

A suitable copolymer is composed of 60% by weight methyl methacrylate, 30% by weight ethyl acrylate and 10% by weight 2-trimethylammoniumethyl methacrylate chloride (EUDRAGIT® RL).

The proportionate amount of the inner coating should be in the range from 2 to 20% by weight based on the core with the active ingredient. It is favorable to use both the above-mentioned copolymer types simultaneously, preferably those with 5 and with 10% by weight 2-trimethylammoniumethyl methacrylate chloride (EUDRAGIT® RS and EUDRAGIT® RL) in a mixture. The mixing ratio can be, for example, 20:1 to 1:20, preferably 10:1 to 1:10.

Outer Coating

The outer coating consists of a copolymer composed of 75 to 95, in particular 85 to 95, % by weight free-radical polymerized $C_1$ to $C_4$-alkyl esters of acrylic or methacrylic acid and 5 to 25, preferably 5 to 15, % by weight (meth)acrylate monomers with an anionic group in the alkyl radical.

$C_1$–$C_4$-alkyl esters of acrylic or methacrylic acid are, in particular, methyl methacrylate, ethyl methacrylate, butyl methacrylate, methyl acrylate, ethyl acrylate and butyl acrylate.

A (meth)acrylate monomer with an anionic group in the alkyl radical can be, for example, acrylic acid, but preferably methacrylic acid.

Particularly suitable (meth)acrylate copolymers are those composed of 10 to 30% by weight methyl methacrylate, 50 to 70% by weight methyl acrylate and 5 to 15% by weight methacrylic acid (EUDRAGIT® FS type).

The proportionate amount of the outer coating should be in the range from 10 to 50% by weight based on the weight of the core with the active ingredient and the inner coating.

The copolymers are obtained in a manner known per se by free-radical bulk, solution, bead or emulsion polymerization. Before processing, they must be brought to the particle size range according to the invention by suitable grinding, drying or spraying processes.

This can take place by simple crushing of extruded and cooled pellets or hot cut.

Preference is given to emulsion polymerization in aqueous phase in the presence of water-soluble initiators and (preferably anionic) emulsifiers (see, for example, DE-C 2 135 073).

The emulsion polymer is preferably produced and used in the form of a 10 to 50 percent by weight, in particular 30 to 40 percent by weight, aqueous dispersion. Partial neutralization of the methacrylic acid units is not necessary for processing; it is, however, possible, for example to the extent of 5 or 10 mol %, if thickening of the coating agent dispersion is desired. The weight-average size of the latex particles is ordinarily 40 to 100 nm, preferably 50 to 70 nm, which ensures a viscosity of below 1 000 mPa·s which is favorable for processing.

The minimum film-forming temperature (MFT in accordance with DIN 53 778) is between 0 and 25° C. for most of the coating agents according to the invention, so that processing is possible at room temperature without added plasticizer. The elongation at break of the films, measured in accordance with DIN 53 455, is ordinarily 50% or more with a triethyl citrate content not exceeding 10% by weight.

Excipients Customary in Pharmacy

To produce the multilayer drug form it is possible to employ excipients customary in pharmacy in the usual way.

Dryers (non-stick agents): Dryers have the following properties: they have large specific surface areas, are chemically inert, are free-flowing and comprise fine particles. Because of these properties, they reduce the tack of polymers containing polar comonomers as functional groups.

Examples of dryers are:

Alumina, magnesium oxide, kaolin, talc, silica (Aerosils), barium sulfate and cellulose.

Release Agents

Examples of release agents are:

esters of fatty acids or fatty amides, aliphatic, long-chain carboxylic acids, fatty alcohols and esters thereof, montan waxes or paraffin waxes and metal soaps; particular mention should be made of glycerol monostearate, stearyl alcohol, glycerol behenic acid ester, cetyl alcohol, palmitic acid, canauba wax, beeswax etc. The usual proportionate amounts are in the range from 0.05% by weight to 5, preferably 0.1 to 3, % by weight based on the copolymer.

Further excipients customary in pharmacy: Mention should be made here of, for example, stabilizers, colorants, antioxidants, wetting agents, pigments, gloss agents etc. They are used in particular as processing aids and are intended to ensure a reliable and reproducible production process and good long-term storage stability. Further excipients customary in pharmacy may be present in amounts from 0.001% by weight to 30% by weight, preferably 0.1 to 10% by weight, based on the copolymer.

Plasticizers: Substances suitable as plasticizers would ordinarily have a molecular weight between 100 and 20 000 and contain one or more hydrophilic groups in the molecule, e.g. hydroxyl, ester or amino groups. Citrates, phthalates, sebacates, castor oil are suitable. Examples of suitable plasticizers are alkyl citrates, glycerol esters, alkyl phthalates, alkyl sebacates, sucrose esters, sorbitan esters, dibutyl sebacate and polyethylene glycols 4 000 to 20 000. Preferred plasticizers are tributyl citrate, triethyl citrate, triethyl acetylcitrate, dibutyl sebacate and diethyl sebacate. The amounts used are between 1 and 35, preferably 2 to 10, % by weight based on the (meth)acrylate copolymer.

Administration Forms

The described drug form can be in the form of a coated tablet, in the form of a tablet composed of compressed pellets or in the form of pellets which are packed in a capsule, for example made of gelatin, starch or cellulose derivatives.

EXAMPLES

Example 1a to 1d

Production of multilayer drug forms consisting of a core with 5-aminosalicylic acid as active ingredient, of an inner coating of a mixture of EUDRAGIT® RS and RL in the ratio 8:2 and of an outer coating of EUDRAGIT® FS in layer thicknesses of 15, 20, 25 and 30% by weight.

Copolymers/polymer Dispersions Employed

EUDRAGIT® RS 30 D: 30% strength aqueous dispersion comprising a copolymer of 65% by weight methyl methacrylate, 30% by weight ethyl acrylate and 5% by weight 2-trimethylammoniumethyl methacrylate chloride.

EUDRAGIT® RL 30 D: 30% strength aqueous dispersion comprising a copolymer of 60% by weight methyl methacrylate, 30% by weight ethyl acrylate and 10% by weight 2-trimethylammoniumethyl methacrylate chloride.

EUDRAGIT® FS 30 D: 30% strength dispersion comprising a copolymer of 25% by weight methyl methacrylate, 65% by weight methyl acrylate and 10% by weight methacrylic acid.

Active-ingredient-containing cores (pellets) were produced in the powder layering process. Employed for this purpose in % by weight were:

| As cores | |
|---|---|
| Nonpareils (0.5–0.6 mm) | 40 g |
| As layering powder | |
| 5-Aminosalicylic acid | 48.75 g |
| Lactose D80 | 10.65 g |
| Aerosil 200 | 0.6 g |
| Total: | 100 g |
| As binders | |
| Kollidon 25 | 5 g |
| Water | 95 g |
| Total: | 100 g |

The cores were sprayed with the binder in a fluidized bed apparatus and the layering powder was added in small portions. Test conditions for the powder layering in detail:

| | |
|---|---|
| Batch size (batch/nonpareils): | 800 g |
| Target size of active ingredient/core: | 975 g |
| Spray gun type: Walter "Bingo" | |
| Spray nozzle diameter: | 1.0 mm |
| Pan speed: | 40 rpm |
| Spray angle (inclination angle pan): | 30° |
| Distance of fluidized bed from spray gun: | 10 cm |
| Spraying pressure: | 0.4 bar |
| Amount of binder (dry) applied: | 13.75 g |
| Binder spraying time: | 70 min |
| Binder spraying rate: | 0.2–0.25 g/min |
| Time (layering) | 66 min |
| Amount per layer | 18 g |
| Drying time in the fluidized bed after application: | 5 min |
| Drying: | 24 h at 40° C. |
| Calculated yield: | 95–98% |

The pellets obtained in this way were dried at 40° C. for 24 hours. Pellets of the 0.7 to 1.0 mm size fraction were then screened out and employed for the sprayed application coating process.

Test conditions for the application of the inner and of the outer copolymer layer in detail:

| | |
|---|---|
| Batch size: | 800 g |
| Spray nozzle diameter: | 1.2 mm |
| Distance of fluidized bed from spray gun: | close |
| Spraying pressure: | 2 bar |
| Amount of air blown in: | 85–95 m³/h |
| Air temperature during this: | 30–40° C. |
| Outlet air temperature: | 26–30° C. |
| Temperature in fluidized bed: | 23–26° C. |
| Spraying rate: | 10 g/min |
| Drying time in the fluidized bed after application: | 5 min |
| Drying: | 24 h at 40° C. |
| Calculated yield: | 96–98% |

Inner Coating Layer

Spray Application

The following mixture was used to apply the inner coating:

| | |
|---|---|
| EUDRAGIT ® RS 30 D | 173 g |
| EUDRAGIT ® RL 30 D | 43 g |
| Glycerol monostearate | 3 g |
| Triethyl citrate | 13 g |
| Tween 80 (33% aq.) | 3 g |
| Water | 173 g |

This results in a spray suspension with a solids content of 20%. The total solid applied to the active ingredient-containing cores was 10.1%, corresponding to 8% by weight polymer.

Outer Coating

Spray Application

| | |
|---|---|
| EUDRAGIT ® FS 30 D | 800 g |
| Glycerol monostearate | 12 g |
| Tween 80 (33% aq.) | 15 g |
| Water | 458 g |

This results in a spray suspension with a solids content of 20%. The total solid applied to the active ingredient-containing cores provided with the inner coating was 32.1%, corresponding to 30% by weight polymer. Cores with a polymer coating corresponding to 15, 20, 25 and, finally, 30% by weight were removed at various times (Examples 1a, 1b, 1c and 1d respectively).

Example 2

Production of multilayer drug forms consisting of a core with 5-aminosalicylic acid as active ingredient from Example 1, of an inner coating of a mixture of EUDRAGIT® RS and RL in the ratio 6.8:3.2 in a layer thickness of 6.8% by weight and of an outer coating of EUDRAGIT® FS in a layer thickness of 14% by weight.

Test conditions for the application of the inner and of the outer copolymer layer in detail:

| | |
|---|---|
| Batch size: | 800 g |
| Spray nozzle diameter: | 1.2 mm |
| Distance of fluidized bed from spray gun: | close |
| Spraying pressure: | 2 bar |
| Amount of air blown in: | 65–85 m³/h |
| Air temperature during this: | 30–40° C. |
| Outlet air temperature: | 26–30° C. |
| Temperature in fluidized bed: | 23–27° C. |
| Spraying rate: | 10 g/min |
| Drying time in the fluirized bed after application: | 5 min |
| Drying: | 24 h at 40° C. |
| Calculated yield: | 95–98% |

Inner Coating Layer

Spray Application

The following mixture was used to apply the inner coating:

| | |
|---|---|
| EUDRAGIT ® RS 30 D | 123 g |
| EUDRAGIT ® RL 30 D | 58 g |
| Glycerol monostearate | 1.5 g |
| Triethyl citrate | 11 g |
| Tween 80 (33% aq.) | 1.5 g |
| Water | 147 g |

This results in a spray suspension with a solids content of 20%. The total solid applied to the active ingredient-containing cores was 8.6%, corresponding to 6.8% by weight polymer.

Outer Coating

Spray Application

| | |
|---|---|
| EUDRAGIT ® ES 30 D | 370 g |
| Glycerol monostearate | 5.5 g |
| Tween 80 (33% aq.) | 2.75 g |
| Water | 218 g |

This results in a spray suspension with a solids content of 20%. The total solid applied to the active ingredient-containing cores provided with the inner coating was 14.9%, corresponding to 14% by weight polymer. (Example 2).

Example 3

Production of multilayer drug forms consisting of a core with 5-aminosalicylic acid as active ingredient from Example 1, of an inner coating of a mixture of EUDRAGIT® RS and RL in t he ratio 8:2 in a layer thickness of 5% by weight and of an outer coating of EUDRAGIT® FS in a layer thickness of 20% by weight.

Test conditions for the application of the inner and of the outer copolymer layer in detail:

| | |
|---|---|
| Batch size: | 800 g |
| Spray nozzle diameter: | 1.2 mm |
| Distance of fluidized bed from spray gun: | close |
| Spraying pressure: | 2 bar |
| Amount of air blown in: | 65–85 m³/h |
| Air temperature during this: | 30–40° C. |
| Outlet air temperature: | 26–30° C. |
| Temperature in fluidized bed: | 23–27° C. |
| Spraying rate: | 10 g/min |
| Drying time in the fluidized bed after application: | 5 min |
| Drying: | 24 h at 40° C. |
| Calculated yield: | 95–98% |

Inner Coating Layer

Spray Application

The following mixture was used to apply the inner coating:

| | |
|---|---|
| EUDRAGIT ® RS 30 D | 106 g |
| EUDRAGIT ® RL 30 D | 27 g |
| Glycerol monostearate | 2 g |
| Triethyl citrate | 8 g |
| Tween 80 (33% aq.) | 2 g |
| Water | 115 g |

This results in a spray suspension with a solids content of 20%. The total solid applied to the active ingredient-containing cores was 6.5%, corresponding to 5% by weight polymer.

Outer Coating

Spray Application

| | |
|---|---|
| EUDRAGIT ® FS 30 D | 533 g |
| Glycerol monostearate | 8 g |
| Tween 80 (33% aq.) | 4 g |
| Water | 315 g |

This results in a spray suspension with a solids content of 20%. The total solid applied to the active ingredient-containing cores provided with the inner coating was 21.5%, corresponding to 20% by weight polymer. (Example 3).

Example 4

Tests of Active Ingredient Release

Method

USP XXIV, method B, modified test for enteric coated products. The test conditions are, in particular: paddle method, 100 revolutions per minute, 37° C.; pH 1.2 with 0.1 N HCl, pH 7.0 by addition of 0.2 M phosphate buffer and adjustment with 2 N NaOH.

Pellets from each of Examples 1a to 1d, and uncoated pellets and pellets provided only with the inner coating as comparison were employed.

200 mg of pellets were placed in 700 ml of 0.1 N HCl in the test apparatus (DT 80, Erweka, Switzerland). After 2 hours, the buffer was changed with 200 ml of 0.2 M phosphate buffer and adjusted to pH 7.0 (Example 1a–d, FIG. 1) or pH 7.5 (Examples 2 and 3, FIG. 2) with 2N HCl or 2N NaOH. The active ingredient release was followed by UV spectrophotometry.

FIG. 1 shows the resulting active ingredient release profiles at pH 7.0:
curve A: uncoated pellets
curve B: pellets provided only with the inner coating
curve C: pellets coated in accordance with Examples 1a to 1d.
Since the release profiles 1a to 1d were virtually identical, they are combined in only one curve.

Result (FIG. 1): The release profiles combined in curve C have a distinctly flatter course than curve B after dissolution of the outer coating layer. The release profile of curve C moreover has a course virtually independent of the thickness of the outer coating layer of the tested pellets 1a to 1d.

Figure 2:
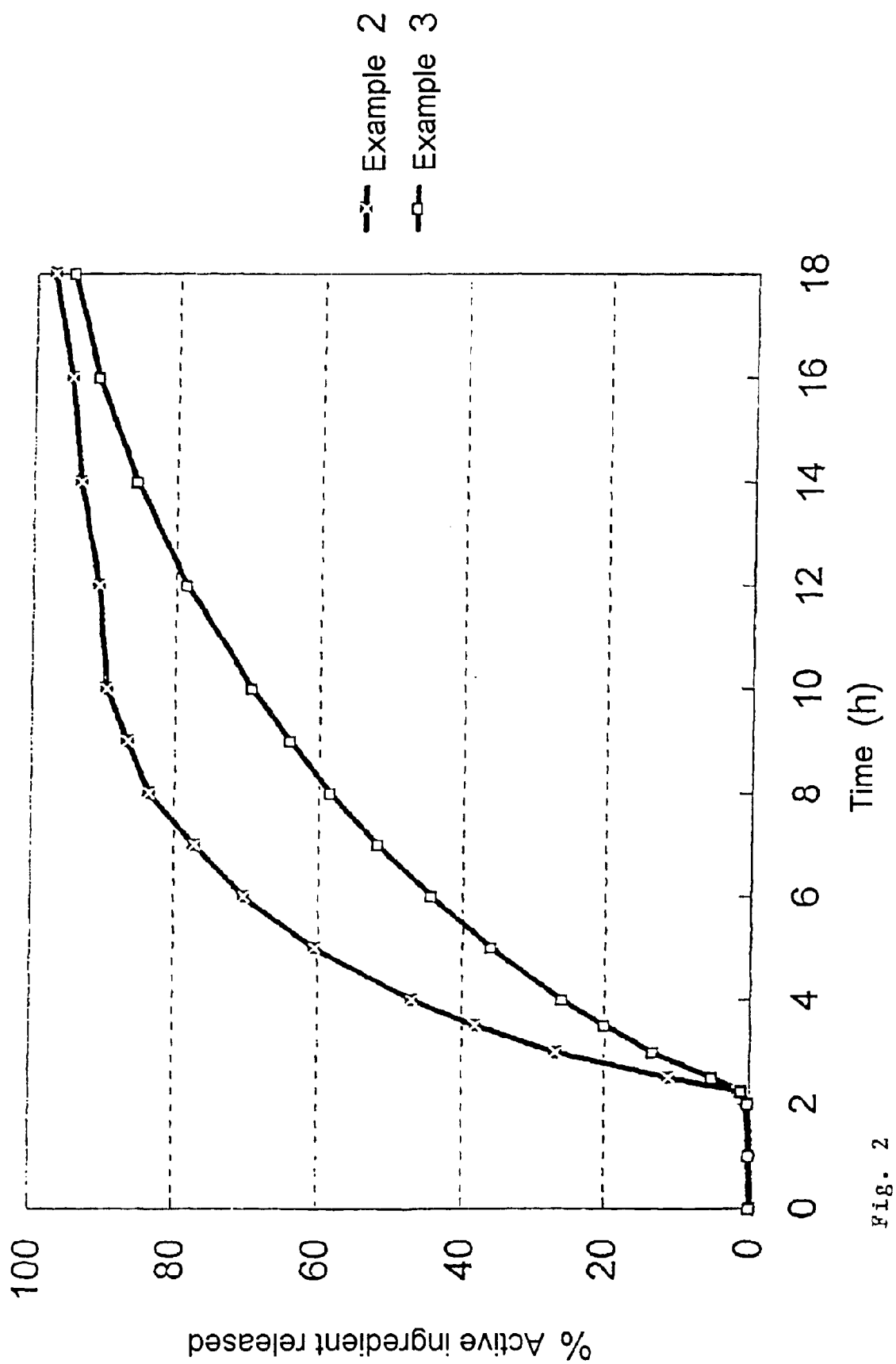

FIG. 2 shows the resulting active ingredient release profiles at pH 7.5:
Example 2: Inner coating of a mixture of EUDRAGIT® RS and RL in the ratio 6.8:3.2 in a layer thickness of 6.8% by weight and an outer coating of EUDRAGIT® FS in a layer thickness of 14% by weight.
Example 3: Inner coating of a mixture of EUDRAGIT® RS and RL in the ratio 8:2 in a layer thickness of 5% by weight and an outer coating of EUDRAGIT® FS in a layer thickness of 20% by weight.

Result (FIG. 2): Delayed active ingredient release takes place even at a pH raised to pH 7.5.

What is claimed is:

1. A multilayer pharmaceutical product comprising:
   a) a core comprising an active pharmaceutical ingredient,
   b) an inner coating of a copolymer or of a mixture of copolymers, said inner coating comprising 85 to 98% by weight free-radical polymerized $C_1$- to $C_4$-alkyl esters of acrylic or methacrylic acid and 15 to 2% by weight (meth)acrylate monomers with a quaternary ammonium group in the alkyl radical, and
   c) an outer coating of a copolymer comprising 75 to 95% by weight free-radical polymerized $C_1$- to $C_4$-alkyl esters of acrylic or methacrylic acid and 5 to 25% by weight (meth)acrylate monomers with an anionic group in the alkyl radical,
   wherein said multilayer pharmaceutical product releases less than 5% of the active pharmaceutical ingredient during the first 2 hours of a USP release test and from 30 to 80% of the active pharmaceutical ingredient 8 hours after the start of the test, wherein the pH of the test is about 1.2 during the first two hours and subsequently the pH is adjusted to about 7.0 by changing a buffer.

2. The multilayer pharmaceutical product claimed in claim 1, wherein the active pharmaceutical ingredient is selected from the group consisting of an aminosalicylate, a sulfonamide and a glucocorticoid.

3. The multilayer pharmaceutical product claimed in claim 2, wherein the active pharmaceutical ingredient is selected from the group consisting of 5-aminosalicylic acid, olsalazine, sulfalazine, prednisone and budesonide.

4. The multilayer pharmaceutical product as claimed in claim 1, wherein the inner coating is from 2 to 50% by weight of the core.

5. The multilayer pharmaceutical product as claimed in claim 1, wherein the outer coating is from 5 to 50% by weight based on the weight of the core and the inner coating.

6. The multilayer pharmaceutical product as claimed in claim 1, wherein the inner coating comprises a mixture of a copolymer A, said copolymer A comprising from 93 to 98% by weight free-radical polymerized $C_1$- to $C_4$-alkyl esters of acrylic or methacrylic acid and from 2 to 7% by weight 2-trimethyl-ammoniumethyl methacrylate chloride, and a copolymer B, said copolymer B comprising from 85 to less than 93% by weight free-radical polymerized $C_1$- to $C_4$-alkyl esters of acrylic or methacrylic acid and from more than 7 to 15% by weight 2-trimethylammoniumethyl methacrylate chloride.

7. The multilayer pharmaceutical product claimed in claim 6, wherein A and B are present in a ratio of from 20:1 to 1:20.

8. The multilayer pharmaceutical product as claimed in claim 1, wherein said multilayer pharmaceutical product is in the form of pellets, tablets compressed from pellets or pellets packed into capsules.

* * * * *